US009828411B2

(12) United States Patent
De Pater et al.

(10) Patent No.: US 9,828,411 B2
(45) Date of Patent: Nov. 28, 2017

(54) METHOD FOR ISOLATING CASPOFUNGIN

(71) Applicant: DSM SINOCHEM PHARMACEUTICALS NETHERLANDS B.V., Delft (NL)

(72) Inventors: Robertus Mattheus De Pater, Echt (NL); Neeraj Tewari, Echt (NL); Roop Singh Yadav, Echt (NL)

(73) Assignee: DSM Sinochem Pharmaceuticals Netherlands B.V., Delft (NL)

( * ) Notice: Subject to any disclaimer, the term of this patent is extended or adjusted under 35 U.S.C. 154(b) by 0 days.

(21) Appl. No.: 14/785,476

(22) PCT Filed: Apr. 28, 2014

(86) PCT No.: PCT/EP2014/058534
§ 371 (c)(1),
(2) Date: Oct. 19, 2015

(87) PCT Pub. No.: WO2014/177483
PCT Pub. Date: Nov. 6, 2014

(65) Prior Publication Data
US 2016/0068564 A1    Mar. 10, 2016

(30) Foreign Application Priority Data

May 2, 2013    (IN) ............................ 1301/DEL/2013
Aug. 29, 2013  (EP) ...................................... 13182208

(51) Int. Cl.
C07K 1/30       (2006.01)
C07K 7/56       (2006.01)

(52) U.S. Cl.
CPC ................ *C07K 1/306* (2013.01); *C07K 7/56* (2013.01); *C07B 2200/13* (2013.01)

(58) Field of Classification Search
None
See application file for complete search history.

(56) References Cited

FOREIGN PATENT DOCUMENTS

| EP | WO 2011/120842 | * 10/2011 | ............... C07K 7/56 |
|----|----------------|-----------|--------------------------|
| WO | WO 97/39763    | 10/1997   |                          |
| WO | WO 2009/142761 | 11/2009   |                          |
| WO | WO 2010/108637 | 9/2010    |                          |
| WO | WO 2012/041801 | 4/2012    |                          |

OTHER PUBLICATIONS

Peters and Timmerhaus, eds., "Plant Design and Economics for Chemical Engineers," 4rth edition, New York: McGraw-Hill, 1991.*
Leonard et al., Journal of Organic Chemistry (2007) 72, 2335-2343.*
International Search Report for PCT/EP2014/058534, dated Jul. 18, 2014, 4 pages.

* cited by examiner

*Primary Examiner* — Karlheinz R Skowronek
*Assistant Examiner* — Catherine Mader
(74) *Attorney, Agent, or Firm* — William D. Hare, Esq.; McNeely, Hare & War, LLP

(57) ABSTRACT

The present invention relates to a method for isolating caspofungin and to a novel crystalline form of caspofungin diacetate thus obtained.

20 Claims, 3 Drawing Sheets

METHOD FOR ISOLATING CASPOFUNGIN

Figure 1:
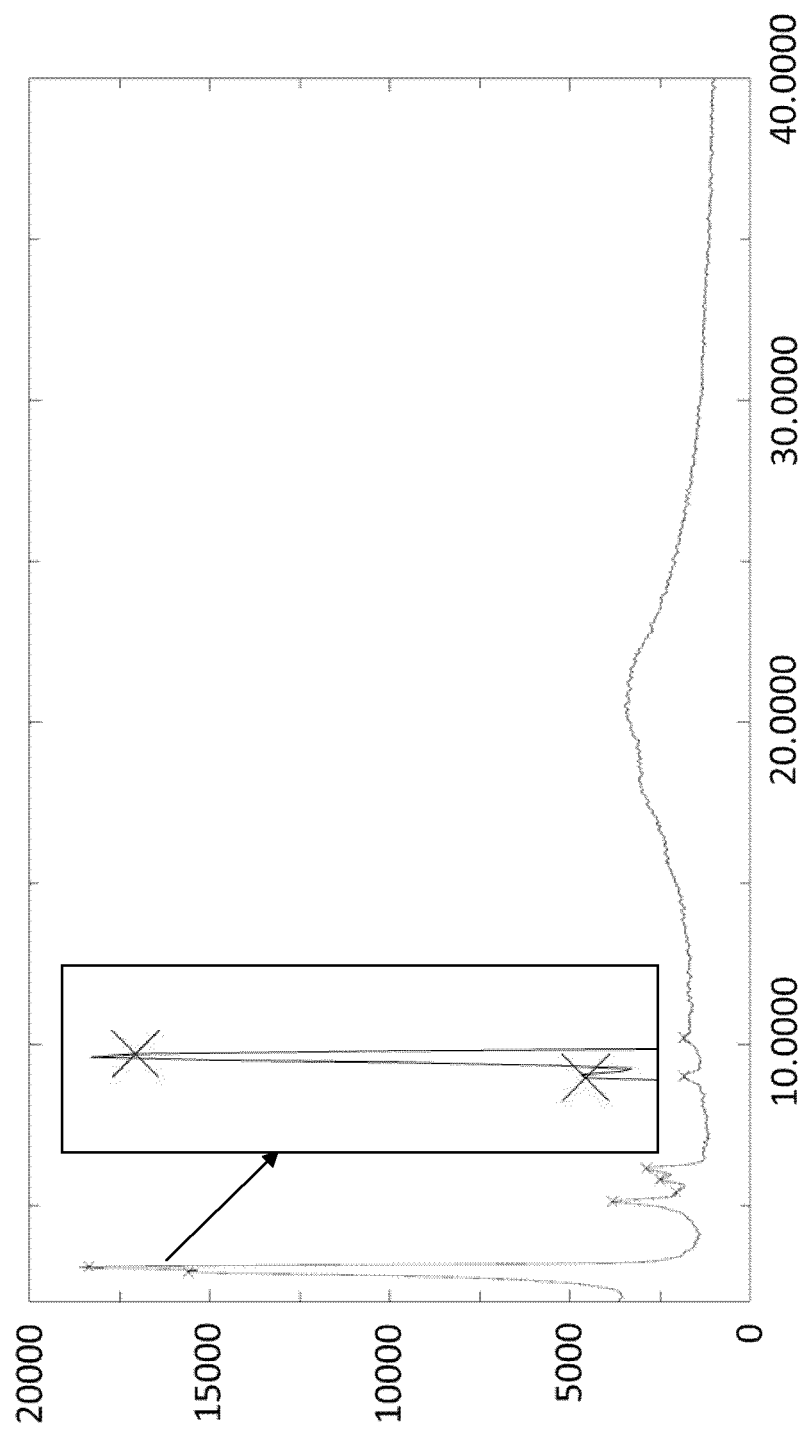

This application is the U.S. national phase of International Application No. PCT/EP2014/058534 filed 28 Apr. 2014, which designated the U.S. and claims priority to EP Patent Application No. 13182208.2 filed 29 Aug. 2013, and IN Patent Application No. 1301/DEL/2013 filed 2 May 2013, the entire contents of each of which are hereby incorporated by reference.

FIELD OF THE INVENTION

The present invention relates to a method for isolating caspofungin and to a novel crystalline form of caspofungin diacetate thus obtained.

BACKGROUND OF THE INVENTION

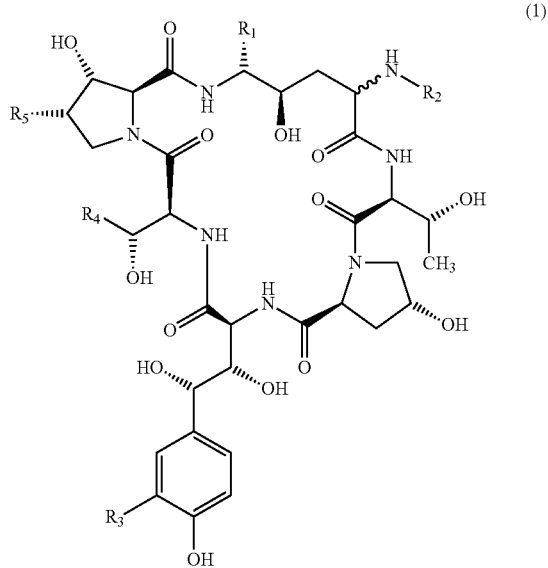

(1)

Cyclopeptides are polypeptides in which the terminal amine and carboxyl groups form an internal peptide bond. Several cyclopeptides are known for their advantageous medicinal properties. An excellent example of this is the class of echinocandins which are potent antifungals. Cyclopeptides can be naturally occurring compounds but may also be obtained by total synthesis or by synthetic or genetic modification of naturally occurring or naturally produced precursors; the latter class is referred to as semi synthetic cyclopeptides. Examples of medicinally useful echinocandins are the cyclohexapeptides anidulafungin, caspofungin, cilofungin and micafungin which are useful in treating fungal infections especially those caused by *Aspergillus, Blastomyces, Candida, Coccidioides* and *Histoplasma*.

Caspofungin (1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$; (1) with $R_1$=—NH(CH$_2$)$_2$NH$_2$, $R_2$=—C(O)(CH$_2$)$_8$CH(CH$_3$)CH$_2$CH(CH$_3$)CH$_2$CH$_3$, $R_3$=—H, $R_4$=—(CH$_2$)$_2$NH$_2$, $R_5$=—H) is a semi synthetic cyclohexapeptide derivable from naturally occurring echinocandins such as for instance echinocandin B, pneumocandin $A_0$ or pneumocandin $B_0$.

Although nature can provide a substantive part of the complex chemical structure of semi synthetic cyclohexapeptides, and in many cases having all chiral centers in the required configuration, a major disadvantage nevertheless is that during fermentation often side products are formed that carry through the process and eventually end up as impurities. Only in few cases can fermentation processes be tuned in such a way as to prevent formation of impurities. Particularly when these impurities are structurally closely related to the main product, their removal is usually tedious and often requires unprecedented purification approaches as the main products in question are chemically unstable and/or prone to racemization.

The preparation of caspofungin (1) from fermentatively obtained pneumocandin $B_0$ is a process wherein removal of impurities is an important issue. A multitude of structurally related impurities occurring during fermentation of pneumocandin $B_0$ has been described. Examples are compounds having an additional methyl function (such as pneumocandin $A_0$, pneumocandin $A_1$, pneumocandin $A_2$, pneumocandin $A_3$, pneumocandin $A_4$, pneumocandin $A_5$, pneumocandin $A_6$), compounds lacking one or two hydroxyl groups (such as pneumocandin $B_1$, pneumocandin $B_2$, pneumocandin $B_5$, pneumocandin $B_6$, pneumocandin $E_0$), compounds having a 4-hydroxy proline rather than a 3-hydroxy proline moiety (pneumocandin $C_0$), compounds having additional hydroxyl groups (such as pneumocandin $D_0$, pneumocandin $D_2$) or the recently described impurity A (US 2009/0324635) wherein, in the caspofungin structure, one of the hydroxy-L-ornithine moieties is replaced by an L-serine moiety.

Recently, in WO 2012/117038 a process was disclosed for preparing azacyclohexapeptide salts using chromatography and crystallization. Although the method is suitable for the laboratory scale preparation of caspofungin of high purity, there remains a need for alternative methods that are industrially applicable, i.e. on larger scale using equipment more appropriate and that yield a product with (more) favorable morphology.

DETAILED DESCRIPTION OF THE INVENTION

In a first aspect of the invention disclosed is a method for isolating caspofungin comprising adding a liquid ester to a solution of caspofungin in an alcohol followed by isolation of the solid material thus obtained, characterized in that said adding is carried out in a stainless steel reactor. Preferably the liquid ester is a solvent such as an acetate, a formate or a propionate of an alcohol such as ethanol, isopropanol, methanol and propanol. Preferred examples are ethyl acetate, isopropyl acetate, methyl acetate and propyl acetate. The alcohol wherein caspofungin is dissolved prior to addition of the liquid ester preferably is an alkyl alcohol wherein the number of carbon atoms is from 1-4, more preferably from 2-3. Preferred alcohols in this respect are ethanol, isopropanol, methanol and propanol.

In a first embodiment, the amount of caspofungin dissolved in an alcohol is of a certain concentration. Since product losses in crystallization processes usually are large attributed to mother liquor losses and the relative amount of mother liquor losses decreases as concentrations increase, it is advantageous to apply a concentration of caspofungin in said alcohol from 3 to 200 g·L$^{-1}$, preferably from 4 to 150 g·L$^{-1}$, more preferably from 5 to 100 g·L$^{-1}$ and most preferably from 10 to 100 g·L$^{-1}$. For optimal yield and product quality the amount of water present in the solution of caspofungin in an alcohol is best kept below 20%, preferably below 10%. A preferred range of water content in the solution of caspofungin in an alcohol is from 0.1% to 20%, preferably from 0.2% to 15%, more preferably from 0.3% to 10%, most preferably from 0.4% to 8%.

In a second embodiment, the method can be carried out in various types of vessels known to the skilled person. Examples are a stainless steel reactor, a glass-lined reactor, a glass reactor and all may be operated in various modes such as the batch reactor model, the continuous stirred-tank reactor model (CSTR) or the plug flow reactor model (PFR). It was surprisingly found that, depending on the type of vessel chosen, caspofungin diacetate of different morphology may be obtained as outlined in the second aspect of the invention. As a result, a novel crystal form (i.e. Form A) having favorable properties in isolation procedures may be obtained by performing the method of the invention in a stainless steel reactor whereas another crystal form (i.e. Form B) is obtained when the method is performed in a glass reactor. The volumes as applied in the various types of vessels are related to the application required. Typically, a glass reactor is suitably used for volumes ranging from 0.05 to 500 L, preferably from 0.1 to 100 L whereas a stainless steel reactor is conveniently used for volumes ranging from 5 to 5000 L, preferably from 10 to 1000 L.

A solution of caspofungin in an alcohol such as ethanol may be conveniently obtained as described in WO 2012/041801.

In a second aspect of the invention there is disclosed crystalline caspofungin diacetate. In one embodiment said crystalline caspofungin diacetate is characterized by data selected from the group consisting of:
(a) An XRD powder diffraction pattern with peaks at 2.91±0.2, 3.07±0.2, 5.09±0.2, 5.38±0.2, 5.78±0.2, 6.12±0.2, 8.96±0.2 and 10.19±0.2 degrees 2-theta;
(b) An XRD powder diffraction pattern as depicted in FIG. 1;
(c) Combinations of (a) and (b).

Suitably the above product, referred to as Form A, can be obtained by performing the method of the first aspect of the invention in a stainless steel reactor. The XRD powder diffraction pattern is further characterized in that the ratio between the intensity of the peak at 3.07±0.2 degrees 2-theta and the intensity of any peak in the region 9.0±0.2 degrees 2-theta is at least 5. Whereas the XRD powder diffraction pattern of crystalline Form A displays peaks at positions different from those of Form B, known from WO 2012/041801, one of the more prominent differences lies in the pattern at around 3.0±0.1 degrees 2-theta: Form B is characterized with a single major peak in this area whereas Form A is characterized by the presence of two major peaks.

Figure 3:
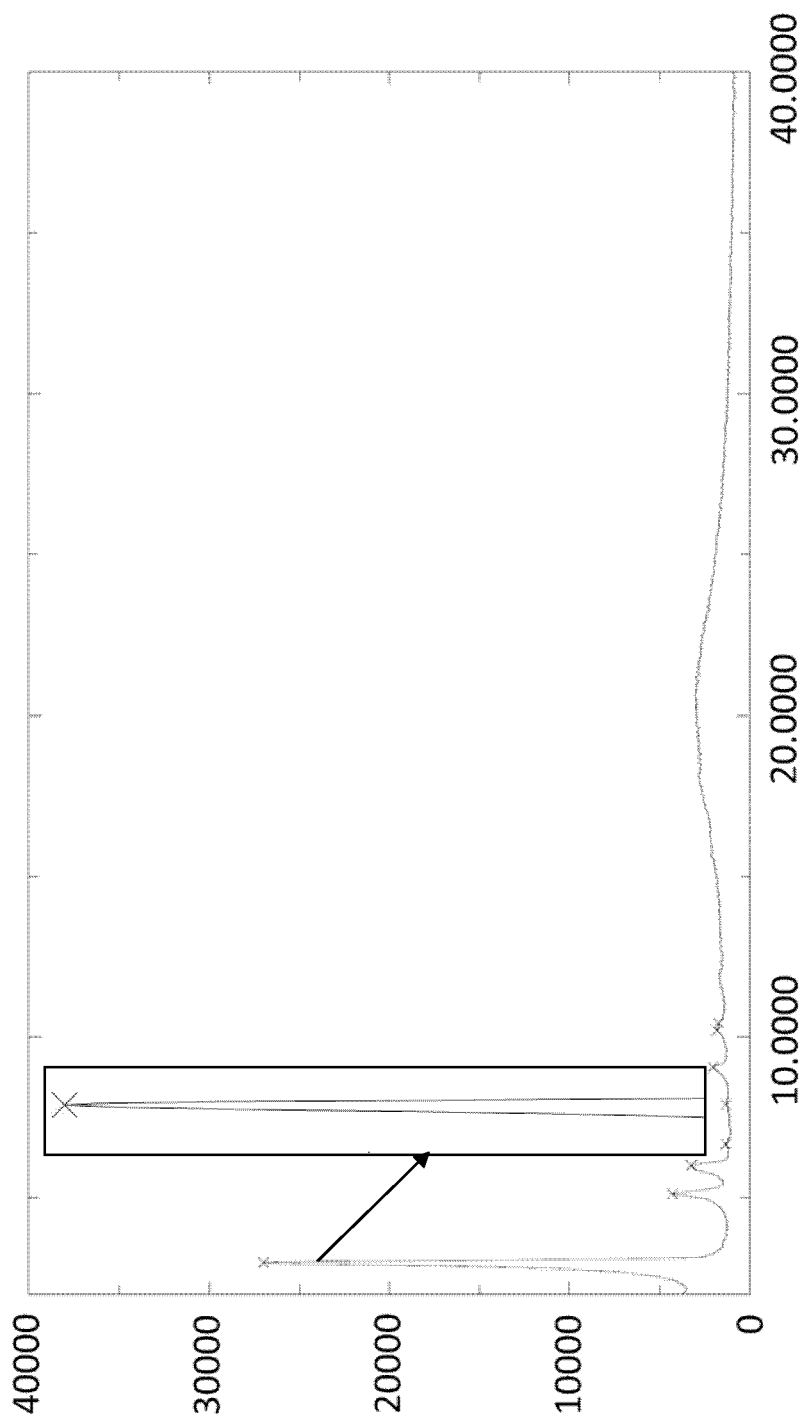

In contrast, when the method of the first aspect of the invention is carried out in a glass reactor, crystalline caspofungin diacetate, referred to as Form B, is obtained with different XRD powder diffraction characteristics selected from the group consisting of:
(a) An XRD powder diffraction pattern with peaks at 2.98±0.2, 5.12±0.2, 6.00±0.2, 6.66±0.2, 7.90±0.2, 9.06±0.2, 10.20±0.2 and 10.42±0.2 degrees 2-theta;
(b) An XRD powder diffraction pattern as depicted in FIG. 3;
(c) Combinations of (a) and (b).

The XRD powder diffraction pattern is further characterized in that the ratio between the intensity of the peak at 2.98±0.2 degrees 2-theta and the intensity of any peak in the region 9.0±0.2 degrees 2-theta is at least 5.

The crystalline compounds of the present invention, i.e. Form A, are of low water content which greatly enhances stability under harsh storage conditions. Thus, the water content of the crystalline caspofungin diacetate of the present invention may be from 0.1% to 10% (w/w). Examples of ranges of water content in the caspofungin diacetate products of the present invention are from 0.1% to 6% (w/w), from 1% to 8% (w/w), from 2 to 6% (w/w) or from 3.5% to 5.5% (w/w). Another advantage of the crystalline compounds of the present invention is improved filterability. The crystalline caspofungin diacetate particles of the present invention, i.e. Form A, are relatively large, thick needles with an average length between about 50-100 μm. The filterability of the crystals is such that isolation by filtration can even be realized by applying mere gravity (i.e. without applying vacuum or pressure over the filtering device). This behavior also facilitates the washing of the crystals after isolation. Mother liquor containing impurities can be removed very efficiently which results in caspofungin diacetate crystals of very high purity. Also important is the ease of drying of the crystals. The drying time of the caspofungin diacetate crystals of the present invention can be very limited, for example only 3 hours under vacuum (at −690 to −710 mm Hg) below 20° C. It is known that caspofungin diacetate can degrade easily under drying conditions. However, as a result of the possibility of the short drying time under mild conditions, the formation of degradation products can be limited to a hitherto unprecedented level.

LEGEND TO THE FIGURES

FIG. 1 is the XRD spectrum of caspofungin diacetate (Form A, Example 1). X-axis: 2-theta value (deg). Y-axis: intensity (cps). The zoomed view indicated by the arrow is the area where the two major peaks at 2.920 and 3.080 degrees can be clearly observed. The following distinct peaks can be discerned:

| Peak no. | 2-Theta (deg) | Flex width | d-Value | Intensity | I/Io |
|---|---|---|---|---|---|
| 1 | 2.920 | 0.118 | 30.2319 | 15599 | 86 |
| 2 | 3.080 | 0.118 | 28.6618 | 18341 | 100 |
| 3 | 5.100 | 0.165 | 17.3131 | 3823 | 21 |
| 4 | 5.400 | 0.141 | 16.3519 | 2055 | 12 |
| 5 | 5.800 | 0.165 | 15.2251 | 2495 | 14 |
| 6 | 6.140 | 0.212 | 14.3827 | 2884 | 16 |
| 7 | 9.000 | 0.282 | 9.8176 | 1839 | 11 |
| 8 | 10.200 | 0.235 | 8.6651 | 1844 | 11 |

Figure 2:
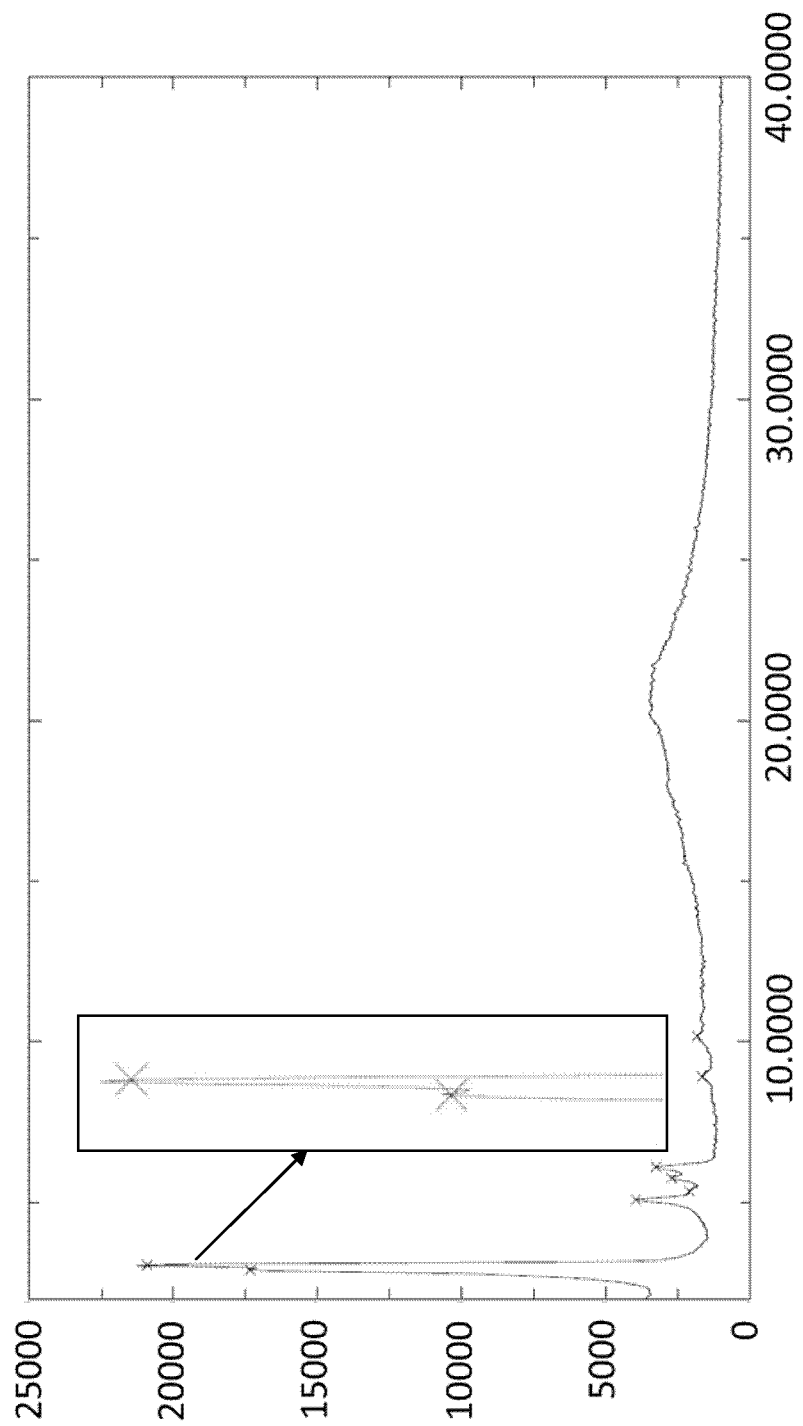

FIG. 2 is the XRD spectrum of caspofungin diacetate (Form A, Example 2). X-axis: 2-theta value (deg). Y-axis: intensity (cps). The zoomed view indicated by the arrow is the area where the two major peaks at 2.920 and 3.060 degrees can be clearly observed. The following distinct peaks can be discerned:

| Peak no. | 2-Theta (deg) | Flex width | d-Value | Intensity | I/Io |
|---|---|---|---|---|---|
| 1 | 2.920 | 0.118 | 30.4404 | 17334 | 83 |
| 2 | 3.060 | 0.118 | 28.8491 | 20913 | 100 |
| 3 | 5.080 | 0.165 | 17.3812 | 3947 | 19 |
| 4 | 5.360 | 0.118 | 16.4739 | 2098 | 11 |
| 5 | 5.760 | 0.165 | 15.3307 | 2715 | 13 |
| 6 | 6.100 | 0.188 | 14.4770 | 3261 | 16 |
| 7 | 8.920 | 0.306 | 9.9055 | 1665 | 8 |
| 8 | 10.180 | 0.141 | 8.6821 | 1829 | 9 |

FIG. 3 is the XRD spectrum of caspofungin diacetate (Form B, Example 3). X-axis: 2-theta value (deg). Y-axis: intensity (cps). The zoomed view indicated by the arrow is the area where only a single peak at 2.980 degrees can be clearly observed. The following peaks can be discerned:

| Peak no. | 2-Theta (deg) | Flex width | d-Value | Intensity | I/Io |
|---|---|---|---|---|---|
| 1 | 2.980 | 0.165 | 29.6234 | 26979 | 100 |
| 2 | 5.120 | 0.165 | 17.2455 | 4287 | 16 |
| 3 | 6.000 | 0.353 | 14.7180 | 3246 | 13 |
| 4 | 6.660 | 0.118 | 13.2609 | 1340 | 5 |
| 5 | 7.900 | 0.094 | 11.1820 | 1305 | 5 |
| 6 | 9.060 | 0.212 | 9.7527 | 2035 | 8 |
| 7 | 10.200 | 0.212 | 8.6651 | 1814 | 7 |
| 8 | 10.420 | 0.094 | 8.4827 | 1722 | 7 |

EXAMPLES

General

X-Ray Powder Diffraction analysis

Samples were analyzed on an Ultima IV X-ray powder diffractometer from Rigaku.

| Source: | X-ray tube | Target: | Cu |
|---|---|---|---|
| Tube Voltage: | 40 kV | Tube Current: | 40 mA |
| Start Angle: | 2 deg | Stop Angle: | 40 deg |
| Scan Axis: | -2 Theta/Theta | Method: | Continuous |
| Counting Units: | CPS (Counts per sec) | Scan Speed: | 2 deg/min |
| Div slit: | -2/3 deg | DHL slit: | -10 mm |
| Scattering slit: | -2/3 deg | Rec slit: | -0.3 mm |

HPLC Analysis
Injection volume: 5 μL
Detection: UV (210 and 270 nm)
Flow: 0.35 mL·min$^{-1}$.
Column: Waters XBridge C18, 3.5 μm, 150 mm*2.1 mm (part no 186003023)
Column temp: 40° C.
Mobile phase A: 50 mM phosphate buffer pH 7 (700 mL)+acetonitrile (300 mL)"
Mobile phase B: 75% acetonitrile
Gradient:

| | Time (min) | | | | | | |
|---|---|---|---|---|---|---|---|
| | 0 | 12 | 15 | 22 | 32 | 34 | 40 |
| % A | 100 | 84 | 84 | 0 | 0 | 100 | 100 |
| % B | 0 | 16 | 16 | 100 | 100 | 0 | 0 |

Solution of Caspofungin in Ethanol

Solutions of caspofungin in ethanol were prepared as follows (see also WO 2012/041801).

A solution of phenylthio pneumocandin $B_0$ amine (1.6 L; 17.3 g phenylthio pneumocandin $B_0$ amine; 15 mmol; 44 vol % water) was cooled to −10° C. Under stirring ethylenediamine (EDA; 320 mL; 4.7 mol) was added in 20 min between −10 and −3° C. Immediately a white precipitate was formed, which dissolved later on. The reaction mixture was stirred for 15 h at 21-22° C. Additional EDA (170 mL; 2.5 mol) was added at 10-20° C. and stirring at ambient temperature was continued for 31 h. Under stirring the reaction mixture and acetic acid (1430 mL; 24.7 mol) were simultaneously added to 1.5 L pre-cooled water of 0° C., keeping the temperature below 10° C. and the pH between 5.1 and 5.5 (quenching is exothermic). At 10° C. and pH 5.3 the mixture was extracted with heptane (2×300 mL). To improve phase separation water (500 mL) was added. The heptane phases were combined and the mix was back-extracted with water (2×250 mL). All aqueous phases were combined and diluted with water to 9.45 L in order to decrease the ethanol content to less than 10%.

Silica gel 100 $C_{18}$ (900 g) was suspended in 75% acetonitrile (2 L). The mixture was placed in a column (height 19.6 cm; internal diameter 10 cm). A bed-volume of 1540 mL was obtained. The column was first washed with three bed-volumes of acetonitrile (100%) and then equilibrated with three bed-volumes aqueous acetic acid (0.15%) with a flow of 80 mL·min$^{-1}$ at approximately 1 bar. The caspofungin solution (9.45 L) as prepared above was used as such for loading on the column. The flow rate was ~50 mL·min$^{-1}$. The flow was adjusted to keep the pressure below 5 bar. The linear flow rate was ~0.6 cm·min$^{-1}$. The loading capacity was 10 g caspofungin diacetate per L resin (12 g total caspofungins per L). Next, the column was washed with aqueous acetic acid (0.15%, 3.2 L) with a flow rate of 70 mL·min$^{-1}$ after which the column was eluted with different solvent compositions at the same flow rate:

10% Acetonitrile/0.15% acetic acid (15 L; 9.7 bed volumes)
13% Acetonitrile/0.15% acetic acid (6375 mL; 4.1 bed volumes)
20% Acetonitrile/0.15% acetic acid (7125 mL; 4.6 bed volumes)

The column was regenerated by washing with 75% acetonitrile/0.15% acetic acid (5625 mL; 3.7 bed volumes). The eluate was monitored continuously with UV (280 nm and 254 nm) and fractions 37-69 were pooled, giving a caspofungin solution of 12.4 L with a yield of 94.7% and a concentration of caspofungin-diacetate of 1.2 g·L$^1$ (based on yield and input before column step). The mass balance of caspofungin over all fractions was 99.1%.

Next, a column with a diameter of 10 cm was filled with Amberchrom XT30 resin giving a bed volume of 628 mL and a bed height of 8 cm. The column was equilibrated with 0.15% acetic acid. Loading, washing, and elution were carried out in two subsequent runs. After the first run the column was equilibrated with 0.15% acetic acid. The eluate was monitored continuously with UV (280 nm and 254 nm). The caspofungin solution (12.4 L) as prepared above was diluted to 30 L with 0.15% acetic acid (=feed).

Loading 1: Caspofungin feed (21 L) was loaded up-flow on the column (16.7 g caspofungin per L resin) with a flow rate of 80 mL·min$^{-1}$). The linear flow rate was 1.0 cm·min$^{-1}$. The pressure did not exceed 2.5 bar.

Washing 1: The column was washed in down-flow with 0.15% acetic acid (1660 mL).

Elution 1: The column was eluted down-flow with ethanol/0.15% acetic acid (1000 mL). Fractions of 200 mL were collected starting from the point where the UV signal started to rise (after approximately 1 bed volume) and analyzed by HPLC and by Karl-Fischer for water analysis (Table 1).

TABLE 1

Results of column run 1

| | | | Water | | Caspofungin | | |
|---|---|---|---|---|---|---|---|
| Fraction | Dilution | Volume (mL) | % (v/v) | Area | Total Area | Yield (%) | Cum. Yield (%) |
| Feed | 1 | 21000 | — | 110.6 | 2323104 | 100 | 100 |
| 1 | 100 | 200 | 22.6 | 84.6 | 1691540 | 72.8 | 72.8 |
| 2 | 100 | 200 | 3.5 | 21.5 | 430940 | 18.6 | 91.4 |
| 3 | 20 | 200 | 0.3 | 9.7 | 38680 | 1.7 | 93.0 |

TABLE 1-continued

Results of column run 1

| Fraction | Dilution | Volume (mL) | Water % (v/v) | Area | Caspofungin Total Area | Yield (%) | Cum. Yield (%) |
|---|---|---|---|---|---|---|---|
| 4 | 10 | 200 | n.d. | 15.2 | 30416 | 1.3 | 94.3 |
| 5 | 10 | 200 | n.d. | 13.6 | 27248 | 1.2 | 95.5 |

The column was equilibrated with 0.15% acetic acid.

Loading 2: Caspofungin feed (10.345 L) was loaded up-flow on the column (8 g caspofungin per L resin) with a flow rate of 70 mL·min$^{-1}$). The linear flow rate was 0.9 cm·min$^{-1}$. The pressure did not exceed 2.5 bar.

Washing 2: The column was washed up-flow with 0.15% acetic acid (947 mL).

Elution 2: The column was eluted down-flow with ethanol/ 0.15% acetic acid (735 mL). Fractions were collected starting from the point where the UV signal started to rise (after approximately 1 bed volume) and analyzed by HPLC and by Karl-Fischer for water analysis (Table 2).

TABLE 2

Results of column run 2

| Fraction | Dilution | Volume (mL) | Water % (v/v) | Area | Caspofungin Total Area | Yield (%) | Cum. Yield (%) |
|---|---|---|---|---|---|---|---|
| Feed | 1 | 10345 | — | 77.0 | 796948 | 100 | 100 |
| 1 | 100 | 105 | 26.6 | 54.7 | 574833 | 72.1 | 72.1 |
| 2 | 20 | 100 | 2.7 | 55.9 | 111710 | 14.0 | 86.1 |
| 3 | 5 | 94 | n.d. | 102.4 | 48136 | 6.0 | 92.2 |
| 4 | 5 | 113 | n.d. | 58.9 | 33291 | 4.2 | 96.4 |
| 5 | 1 | 113 | n.d. | 86.3 | 9757 | 1.2 | 97.6 |
| 6 | 1 | 210 | n.d. | 18.0 | 3782 | 0.5 | 98.1 |

Fractions 1 up to and including 5 of both runs were pooled, giving 1525 mL of a caspofungin solution with an estimated concentration of 9.5 g·L$^1$ (based on yield and input before both runs). The overall yield over both runs was 96.2%. The water concentration of the pooled fractions was analyzed by Karl-Fischer: 5.5%.

The solution obtained above (see Table 3) was used as such for crystallization.

TABLE 3

HPLC results of caspofungin solution after concentration and solvent switch

| Peak no. | Retention time (min) | Peak name | Height (mAU) | Area (mAU * min) | Rel. Area (%) |
|---|---|---|---|---|---|
| 1 | 2.21 | | 1.193 | 0.254 | 0.23 |
| 2 | 9.43 | | 0.003 | 0.020 | 0.02 |
| 3 | 10.23 | | 0.001 | 0.028 | 0.03 |
| 4 | 10.99 | | 0.001 | 0.018 | 0.02 |
| 5 | 12.17 | | 0.579 | 0.160 | 0.14 |
| 6 | 12.68 | Caspofungin | 226.299 | 109.042 | 98.43 |
| 7 | 20.76 | | 3.843 | 0.852 | 0.77 |
| 8 | 21.19 | | 0.007 | 0.327 | 0.29 |
| 9 | 22.73 | | 0.583 | 0.076 | 0.07 |

Example 1

Caspofungin Crystallization in Stainless Steel Reactor

The crystallization was started with 29 L of a caspofungin solution in ethanol (13.6 g·L$^{-1}$; 394 g caspofungin) containing 6.1 w/w % water and 0.4% acetic acid, obtained as outlined in the General section. The caspofungin solution was charged into a stainless steel reactor of 350 L, equipped with an anchor type stirrer. Under stirring ethyl acetate (19 L) was slowly added in about 3 hours at about 20° C. and stirring was continued for 1 hour allowing crystals to form. Next ethyl acetate (38 L) was slowly added in 12 hours. After stirring at about 20° C. for another 2 hours, the crystals were successively filtered off by centrifugation, washed two times with ethyl acetate/ethanol/water (62.5/35.5/2 (v/v/v), 3.6 L), washed with ethyl acetate (two times 2 L), and dried under vacuum yielding 224 g caspofungin as white crystals (Form A, FIG. 1).

Example 2

Caspofungin Crystallization in Stainless Steel Reactor

The crystallization was started with 32.5 L of a caspofungin solution in ethanol (12.9 g·L$^{-1}$; 419 g caspofungin) containing 7.6 w/w % water and 0.4% acetic acid, obtained as outlined in the General section. The caspofungin solution was charged into a stainless steel reactor of 350 L, equipped with an anchor type stirrer. Under stirring ethyl acetate (25 L) was slowly added in about 4.5 hours at about 20° C. Stirring was continued at about 20° C. for 1 hour allowing crystals to form. Next ethyl acetate (29 L) was slowly added in 12 hours. After stirring at about 20° C. for another 2 hours, the crystals were successively filtered off by centrifugation, washed two times with ethyl acetate/ethanol/water (62.5/35.5/2 (v/v/v), 4.4 L), washed with ethyl acetate (two times 2 L), and dried under vacuum yielding 303 g caspofungin as white crystals (Form A, FIG. 2).

Example 3

Caspofungin Crystallization in Glass Round Bottom Flask

The crystallization was started with 400 mL of a caspofungin solution in ethanol (13.6 g·L$^{-1}$; 5.44 g caspofungin) containing 6.1 w/w % water and 0.4% acetic acid, obtained as outlined in the General section. The caspofungin solution was charged into a 2 L glass three necked round bottom flask equipped with a glass stirrer. Under stirring ethyl acetate (240 mL) was slowly added in about 3 hours at about 20° C. and stirring was continued for 1 hour allowing crystals to form. Next ethyl acetate (420 mL) was slowly added in 12 hours. After stirring at about 20° C. for another 2 hours, the crystals were successively filtered off, washed three times with ethyl acetate/ethanol/water (62.5/35.5/2 (v/v/v), 50 mL), washed with ethyl acetate (three times 50 mL) and dried under vacuum, yielding 4.0 g caspofungin as white crystals (Form B, FIG. 3).

The invention claimed is:
1. Method for isolating caspofungin diacetate comprising adding a liquid ester to a solution of caspofungin in an alcohol followed by isolation of the solid material thus obtained, wherein said adding is carried out in a stainless steel reactor.

2. Method according to claim 1 wherein said liquid ester is chosen from the group consisting of ethyl acetate, isopropyl acetate, methyl acetate and propyl acetate and said alcohol is chosen from the group consisting of ethanol, isopropanol, methanol and propanol.

3. Method according to claim 1 wherein the concentration of caspofungin in said alcohol is from 5 to 100 g·$L^{-1}$.

4. Method according to claim 3 wherein the volume of said solution of caspofungin in an alcohol is from 10 to 1000 L.

5. Method according to claim 1 wherein the amount of water in said solution of caspofungin in an alcohol is less than 10%.

6. Crystalline caspofungin diacetate, wherein the crystalline caspofungin diacetate has x-ray powder diffraction data selected from the group consisting of:
    (a) An XRD powder diffraction pattern with peaks at 2.91±0.2, 3.07±0.2, 5.09±0.2, 5.38±0.2, 5.78±0.2, 6.12±0.2, 8.96±0.2 and 10.19±0.2 degrees 2-theta; and
    (b) An XRD powder diffraction pattern as depicted in FIG. 1.

7. Crystalline caspofungin diacetate according to claim 6 wherein a ratio between the intensity of said peak at 3.07±0.2 degrees 2-theta and the intensity of any peak in the region 9.0±0.2 degrees 2-theta is at least 5.

8. Crystalline caspofungin diacetate according to claim 6 wherein the water content of the crystalline caspofungin diacetate is from 0.1% to 8% (w/w).

9. Crystalline caspofungin diacetate according to claim 6 wherein the water content of the crystalline caspofungin diacetate is from 0.1% to 10% (w/w).

10. Crystalline caspofungin diacetate according to claim 6 wherein the water content of the crystalline caspofungin diacetate is from 2% to 6% (w/w).

11. Crystalline caspofungin diacetate according to claim 6 wherein the crystalline caspofungin diacetate has a x-ray powder diffraction pattern with peaks at 2.91±0.2, 3.07±0.2, 5.09±0.2, 5.38±0.2, 5.78±0.2, 6.12±0.2, 8.96±0.2 and 10.19±0.2 degrees 2-theta.

12. The method for isolating caspofungin according to claim 1, wherein the isolated caspofungin diacetate has a x-ray powder diffraction pattern with peaks at 2.91±0.2, 3.07±0.2, 5.09±0.2, 5.38±0.2, 5.78±0.2, 6.12±0.2, 8.96±0.2 and 10.19±0.2 degrees 2-theta.

13. The method for isolating caspofungin according to claim 1, wherein the isolated caspofungin diacetate has a x-ray powder diffraction pattern as depicted in FIG. 1.

14. A method for isolating crystalline caspofungin diacetate comprising:
    adding a liquid ester to a solution of caspofungin in an alcohol in a stainless steel vessel; and
    isolating the solid material thus obtained as crystalline caspofungin diacetate,
    wherein the crystalline caspofungin diacetate has an XRD powder diffraction pattern with peaks at 2.91±0.2, 3.07±0.2, 5.09±0.2, 5.38±0.2, 5.78±0.2, 6.12±0.2, 8.96±0.2 and 10.19±0.2 degrees 2-theta.

15. The method according to claim 14, wherein said liquid ester is chosen from the group consisting of ethyl acetate, isopropyl acetate, methyl acetate and propyl acetate and said alcohol is chosen from the group consisting of ethanol, isopropanol, methanol and propanol.

16. The method according to claim 14, wherein the concentration of caspofungin in said alcohol is from 5 to 100 g·$L^{-1}$.

17. The method according to claim 16, wherein the volume of said solution of caspofungin in an alcohol is from 10 to 1000 L.

18. The method according to claim 14, wherein the amount of water in said solution of caspofungin in an alcohol is less than 10%.

19. The method according to claim 14, wherein a ratio between the intensity of the peak at 3.07±0.2 degrees 2-theta and the intensity of any peak in the region 9.0±0.2 degrees 2-theta is at least 5.

20. The method according to claim 14, wherein the water content of the crystalline caspofungin diacetate is from 0.1% to 8% (w/w).

* * * * *